United States Patent [19]

Fussell

[11] Patent Number: 5,392,379
[45] Date of Patent: Feb. 21, 1995

[54] ELECTRICALLY ACTIVATED AROMATIC ORNAMENT

[75] Inventor: David A. Fussell, St. Augustine, Fla.
[73] Assignee: Ornamotor, Inc., Duluth, Ga.
[21] Appl. No.: 255,059
[22] Filed: Jun. 7, 1994
[51] Int. Cl.⁶ .......................... F24F 6/08; A61L 9/03
[52] U.S. Cl. .................................. 392/390; 239/51.5;
239/56; 428/10; 428/905
[58] Field of Search ............... 392/390, 392, 393, 403,
392/404; 239/53, 55, 56, 57, 60, 51.5; 362/122,
123; 428/7, 10, 905

[56] References Cited

U.S. PATENT DOCUMENTS

| | | | |
|---|---|---|---|
| 2,657,090 | 10/1953 | Meek | 239/55 |
| 3,220,913 | 11/1965 | Thomas | 239/51.5 |
| 3,698,991 | 10/1972 | Susewitz | 428/905 |
| 3,945,568 | 3/1976 | Bychowski | 428/905 |
| 4,361,279 | 11/1982 | Beacham | 239/56 |
| 4,695,435 | 9/1987 | Spector | 239/55 |
| 4,890,791 | 1/1990 | Hoffman | 239/57 |

Primary Examiner—Teresa J. Walberg
Attorney, Agent, or Firm—James A. Hinkle

[57] ABSTRACT

An aroma generator has a toroidal incense container with a toroidal channel and cylindrical walls. A toroidal channel floor is extended in a plane perpendicular to an axis that is common to the cylindrical walls of the toroidal channel. A bulb-attachment wall having a central bulb orifice is extended inward radially at a design distance from a base of the toroidal incense container. A cover plate is held in a covering position over the toroidal channel by attachment appendages on a cylindrical attachment sleeve. At least one attachment appendage is extended outward radially from a distal end of the cylindrical attachment sleeve and positioned in at least one arcuate attachment channel in an outside surface of the inside cylindrical wall for attachment of the cover plate to the aroma generator. A plurality of spacer ridges are extended radially from the cover plate to provide aroma-discharge passages between the cover plate and top edges of the toroidal channel. A resistance heater is positioned in the channel floor and optionally in channels walls to activate emission of aroma from toroidal incense material positioned in the toroidal channel. The resistance heater can be divided into segments to protect structural integrity. An approximately hemispherical light dome is positioned centrally on the cover plate and extended in an opposite direction from the cylindrical attachment sleeve. A toroidal bulb socket made of rubber or rubber-like material is extended inward radially from the bulb-attachment wall. A Christmas tree light bulb or other similar light bulb can be inserted in the toroidal bulb socket and extended into the light dome on the cover plate.

26 Claims, 2 Drawing Sheets

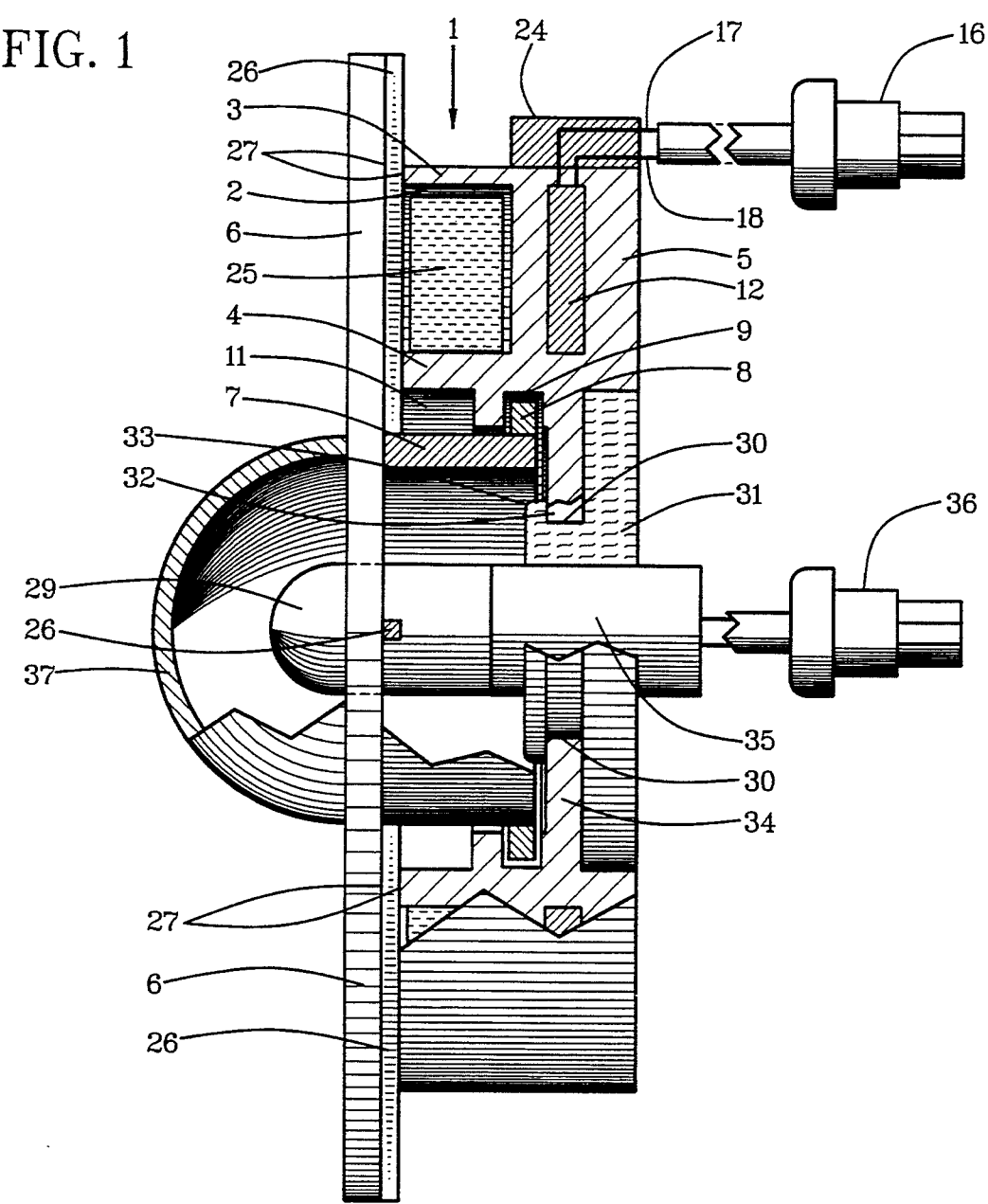
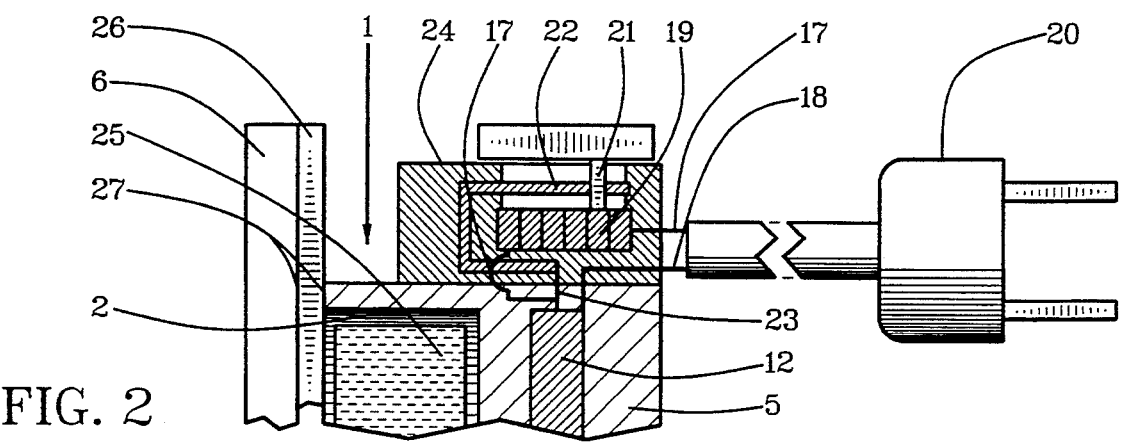

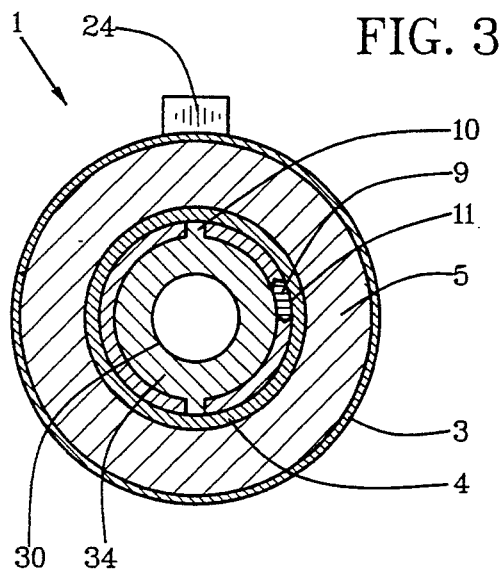
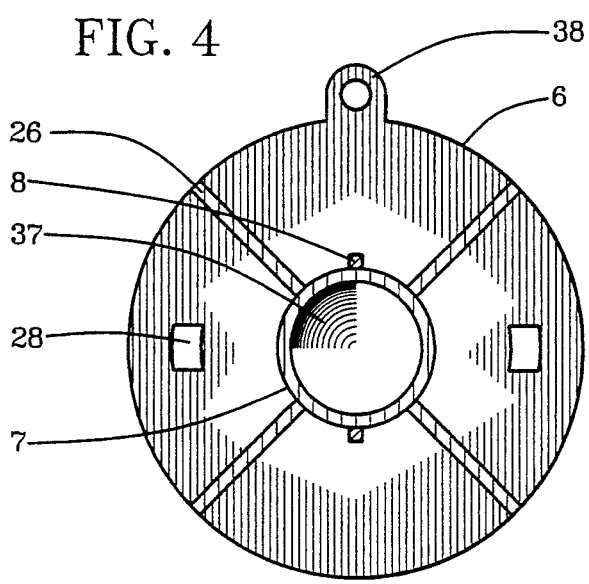
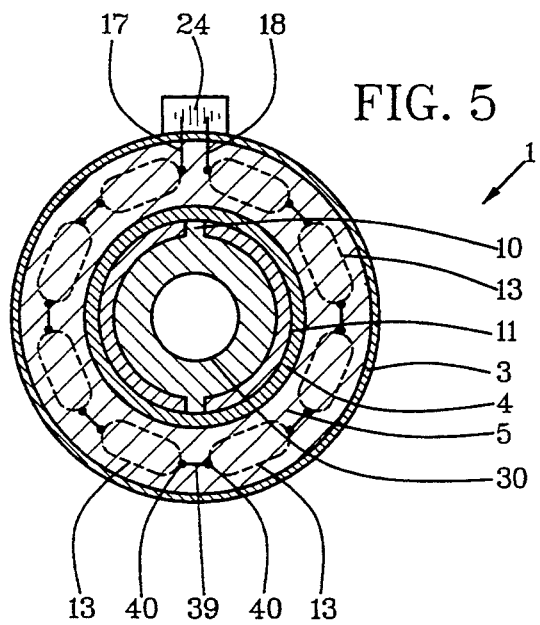
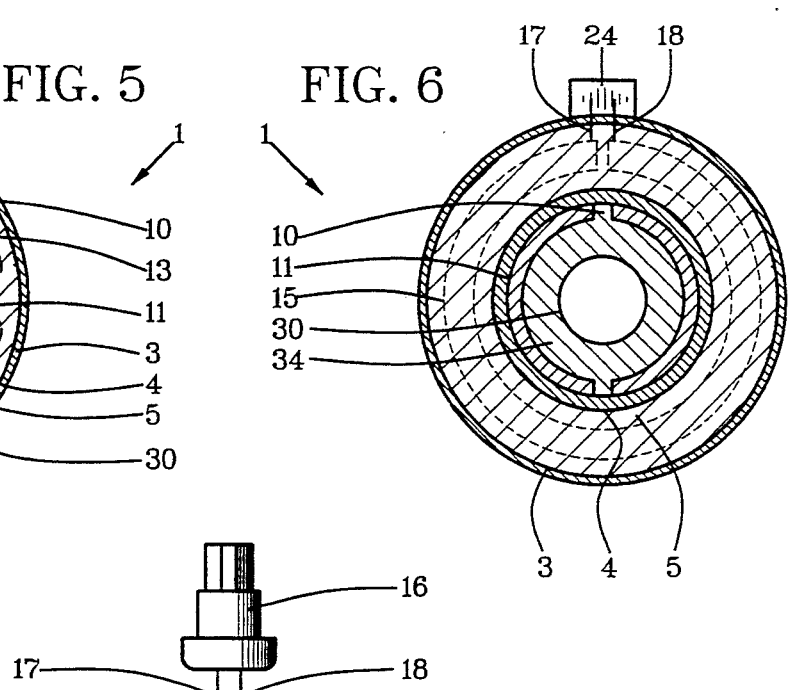
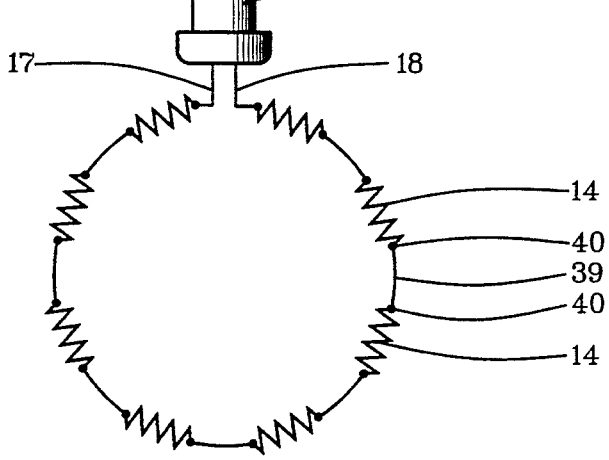

ELECTRICALLY ACTIVATED AROMATIC ORNAMENT

BACKGROUND OF THE INVENTION

I. Field of the Invention

The present invention relates generally to the field of devices for generating aroma that are attachable to aromatic ornaments such as Christmas tree ornaments, wreaths, bouquets of artificial flowers and other items that are suggestive of having an aroma.

II. Description of the Prior Art

There have been aroma generators that are activated by heat from electrical current independently of any ornament. There also have been ornaments that are aroma generators. But there are no known aroma generators that are attachable conveniently to a variety of ornaments as taught by this invention.

An ornament that is an aroma generator was taught by the same inventor, David A. Fussell, in U.S. Pat. No. 5,233,680 granted Aug. 3, 1993. Being itself an ornament, instead of an aroma generator attachable to a variety of ornaments, that invention was limited to the particular ornaments described. It could not be used conveniently and effectively for attachment to, for insertion into or for positioning on a wide variety of ornaments or other objects as taught by this invention. That invention was constructed to provide and was limited to providing both aromatic qualities and particular aesthetic structures in wreath forms. This invention is not limited to use as a component of particular aesthetic structures such as wreaths. Instead, it can be attached to a wide variety of objects which provide aesthetic characteristics separately. A wreath is only one of numerous structures or objects with which this aroma generator can be used conveniently, advantageously and effectively. Consequently, it is distinctly different from the previous Fussell patent cited above.

SUMMARY OF THE INVENTION

In accordance with the present invention, it is contemplated that in light of inability to use prior-art aroma generators with various present ornaments and the limitations of prior aromatic ornaments to their particular ornamental structures, objects of this invention are to provide an aroma generator which:

- Is attachable conveniently to a wide variety of ornaments and ornamental structures;
- Is attachable to a wide variety of objects which are not ornaments but from which aroma is desired to be emitted;
- Is light and shaped for convenient attachment to a wide variety of objects;
- Uses low electrical power from such sources as Christmas tree light sockets;
- Has a Christmas tree light holder for illumination in addition to generation of aroma;
- Has variable consumption of electrical current for different use conditions;
- Provides channels for effective emission of aromas generated; and
- Uses standard sizes of toroidal incense materials.

This invention accomplishes the above and other objectives with an aroma generator having a toroidal incense container with a toroidal channel and cylindrical walls. A toroidal channel floor is extended in a plane perpendicular to an axis that is common to the cylindrical walls of the toroidal channel. A bulb-attachment wall having a central bulb orifice is extended inward radially at a design distance from a base of the toroidal incense container. A cover plate is held in a covering position over the toroidal channel by attachment appendages on a cylindrical attachment sleeve. At least one attachment appendage is extended outward radially from a distal end of the cylindrical attachment sleeve and positioned in at least one arcuate attachment channel in an outside surface of the inside cylindrical wall for attachment of the cover plate to the aroma generator. A plurality of spacer ridges are extended radially from the cover plate to provide aroma-discharge passages between the cover plate and top edges of the toroidal channel. A resistance heater is positioned in the channel floor and optionally in channels walls to activate emission of aroma from toroidal incense material positioned in the toroidal channel. The resistance heater can be divided into segments to protect structural integrity. An electrical line is extended from a plug of a desired size to the resistance heater. A variable resistor can be provided for regulation of current for various heat requirements and for desired different rates of aromatic discharge from the incense material. An approximately hemispherical light dome is positioned centrally on the cover plate and extended in an opposite direction from the cylindrical attachment sleeve. A toroidal bulb socket made of rubber or rubber-like material is extended inward radially from the bulb-attachment wall. A Christmas tree light bulb or other similar light bulb can be inserted in the toroidal bulb socket and extended into the light dome on the cover plate.

Other objects, advantages and capabilities of the invention will become apparent from the following description taken in conjunction with the accompanying drawings showing preferred embodiments of the invention

BRIEF DESCRIPTION OF THE DRAWINGS

FIG. 1 is a cutaway side view of an assembled unit containing a fragrance cartridge;

FIG. 2 is a cutaway sectional view of a variable heat control that is optional;

FIG. 3 is a front view of a toroidal incense container;

FIG. 4 is a rear view of a cover plate for the toroidal incense container;

FIG. 5 is the FIG. 3 illustration with a segmented heater element;

FIG. 6 is the FIG. 3 illustration with a unitary heater element; and

FIG. 7 is a wiring diagram of the FIG. 5 illustration.

DESCRIPTION OF THE PREFERRED EMBODIMENTS

Referring to the drawings wherein like reference numerals designate corresponding parts throughout the several figures, a preferred embodiment is shown in FIG. 1. A toroidal fragrance container 1 has a toroidal container channel 2 with a cylindrical outside wall 3, a cylindrical inside wall 4 and a channel base 5 extended between the cylindrical outside wall 3 and the cylindrical inside wall 4. A cover plate 6 in a covering position over the toroidal container channel 12 has a cylindrical attachment sleeve 7 from which at least one attachment appendage 8 is extended radially from an attachment end of the cylindrical attachment sleeve 7.

The attachment appendage 8 can be positioned in at least one arcuate attachment channel 9 which has at least one linear entrance 10 to the attachment channel 9 as shown in FIGS. 3, 5 and 6. The attachment appendage 8 and the arcuate attachment channel 9 with the linear entrance 10 are quick-disconnect threading. They allow the cover plate 6 to be attached quickly and easily by merely inserting the cylindrical attachment sleeve 7 into an attachment receptacle 11 in the toroidal fragrance container 1 and then turning the cover plate 6 a part of a rotation. Detachment of the cover plate 6 is achieved just as easily by rotating it part of a rotation in the opposite direction.

An electrical-resistance heater 12 is positioned in the channel base 5 of the toroidal container channel 2. The electrical resistance heater 12 can be comprised of multiple electrical-resistance sections 13 as shown with dashed lines in FIG. 5 and as diagrammed as resistors 14 in FIG. 7. Alternatively, the electrical-resistance heater 12 can be a unitary heater element 15 as represented by dashed lines in FIG. 6. Whether sectioned or unitary, the electrical-resistance heater 12 can be supplied with electrical current by such electrical sources as a Christmas tree light plug 16 having a positive line 17 and a negative line 18.

Optionally as shown in FIG. 2, the positive line 17 can be routed through resistors 19 having a design resistance value to decrease current as desired, particularly if the source of electrical current is a standard residential light plug 20 that is supplied with standard outlet current. Further optional, current can be regulated with variable resistance by positioning a resistor contact 21 in contact with a desired plurality of resistors 19 in series. Current from the resistor contact 21 is then transmitted to a conductor bar 22 which transmits it to a positive line 23 from the conductor bar 22 that is employed for this variable option. For use of the variable option, the portion of the positive line 17 shown in FIG. 2 as an arcuate member bypassing the conductor bar 22, can be omitted. An appropriate connector boss 24 can be positioned on the toroidal fragrance container 1.

Heat from the electrical-resistance heater 12 in either form 13 or 15 activates an aroma cartridge 25 that can be positioned in the toroidal container channel 2 as shown in FIGS. 1 and 2. The amount of heat determines the rate of generation of aroma from an aroma cartridge 25 having a particular volatility for phase-change directly from a solid to a gas form.

As shown in FIGS. 1, 2 and 4, the cover plate 6 has a plurality of spacer ridges 26 which form aroma-discharge passages 27 between the cover plate 6 and tops of the cylindrical channel walls 3 and 4. Also as shown in FIG. 4, plate discharge orifices 28 can be provided in addition to the aroma-discharge passages 27 for discharge of aroma from the aroma cartridge 25.

Further illustrated in FIG. 1, a light bulb 29, generally a Christmas tree light bulb, can be positioned in the attachment receptacle 11 from a bulb-insertion aperture 30 in the toroidal fragrance container 1. For holding light bulbs 29, particularly Christmas tree light bulbs, a grommet 31 made of rubber or rubber-like material is positioned in the insertion aperture 30. The grommet 31 has a circumferential attachment channel 32 with a rounded inside wall 33 that allows the grommet 31 to be forced into the insertion aperture 30, thereby causing rubber-like resilience of the grommet 31 to yield to allow positioning of the grommet 31 on a bulb-attachment wall 34 surrounding the insertion orifice 30. Preferably, bulb base 35 of the light bulb 29 is positioned in contact with the grommet 31. An electrical source for the light bulb 29 is shown as a standard Christmas tree plug and cord 36.

Light from a light bulb 29 can be employed to illuminate an ornament or other object or an area as desired. To protect a light bulb 29 and yet to allow illumination from it, a dome 37 that is transparent may be provided and extended from the cover plate 6 at an opposite side from the cylindrical attachment sleeve 7. The cover plate 6 also can be transparent or translucent to transmit light from the light bulb 29.

For many applications, this aroma generator is positioned in or on various ornaments. However, it may also be hung from a handle 38 as shown in FIG. 4. This allows it to be hung on walls, in cabinets, from shelves, from ceilings and from Christmas trees directly in addition to being positioned wherever else desired. One popular positioning for all occasions at any time can be in, on or amongst bouquets of either artificial or real flowers and potted plants.

The sections 13 of the electrical-resistance heater 12 illustrated with dashed lines in FIG. 5 and diagrammed as resistors 14 in FIG. 7 are joined by conductors 39 intermediate connections 40. This minimizes heat between the sections 13 and 14.

Various modifications may be made of the invention without departing from the scope thereof and it is desired, therefore, that only such limitations shall be placed thereon as are imposed by the prior art and which are set forth in the appended claims.

What is claimed is:

1. An aroma generator comprising a toroidal fragrance container having a toroidal container channel with a cylindrical inside wall, a cylindrical outside wall positioned a select distance outward radially from the cylindrical inside wall and a channel base extended radially intermediate a bottom of the inside wall and a bottom of the cylindrical outside wall, a cover plate maintained in a covering position over the toroidal container channel with a cylindrical attachment sleeve extended from a container side of the cover plate, at least one attachment appendage extended outward radially from an attachment end of the cylindrical attachment sleeve, at least one arcuate attachment channel on an outside periphery of the cylindrical inside wall has a linear entrance into which the attachment appendage is positioned and then rotated about the axis of the toroidal fragrance container by rotation of the cover plate to position the attachment appendage in the arcuate attachment channel where a wall of the arcuate attachment channel is intermediate the attachment appendage and the cover plate to prevent linear removal of the cover plate without opposite rotation before linear removal, an electrical-resistance heater in the channel base, and a plurality of spacer ridges positioned radially on an attachment side of the cover plate to provide aroma-discharge passages between the cover plate and top edges of the toroidal channel.

2. An aroma generator as claimed in claim 1 and further comprising a means for attaching a light bulb of a select size to the toroidal fragrance container at a position radially inward from the cylindrical inside wall of the toroidal container channel with an attachment stem of the light bulb extended outward from the toroidal fragrance container for attachment to a light-bulb socket linearly to the axis of the toroidal fragrance container.

3. An aroma generator as claimed in claim 2, wherein the means for attaching a light bulb of a select size to the toroidal fragrance container is a rubber grommet having an attachment aperture sized and shaped to receive the stem of the light bulb with desired tightness, and an outside periphery of the rubber grommet is attachable to an inside periphery of the toroidal fragrance container proximate a base end of the toroidal container channel.

4. An aroma generator as claimed in claim 2 and further comprising a bulb-attachment wall positioned at a design distance inward linearly from the base end of the toroidal container channel and extended inward radially a design distance to a bulb-attachment aperture,
   a rubber grommet positioned adjacent to the bulb-attachment wall and the inside periphery of the toroidal fragrance container, and
   a bulb-attachment aperture in the rubber grommet having an inside periphery concentric to the axis of the toroidal fragrance container for concentric positioning and retainment of the light bulb linearly to the axis of the toroidal fragrance container.

5. An aroma generator as claimed in claim 1 and further comprising a means for safety protection against heat and breakage of a light bulb positioned centrally in the torodial fragrance container.

6. An aroma generator as claimed in claim 5, wherein the means for protection against heat and breakage of the light bulb positioned centrally in the torodial fragrance container is as a dome extended centrally from a side opposite the container side of the cover plate, and an open side of the dome is sized and shaped to receive a design portion of a light bulb positioned centrally in a base end of the torodial fragrance container.

7. An aroma generator as claimed in claim 4 and further comprising a means for safety protection against heat and breakage of a light bulb positioned centrally in the torodial fragrance container.

8. An aroma generator as claimed in claim 7, wherein the means for protection against heat and breakage of the light bulb positioned centrally in the torodial fragrance container is as a dome extended centrally from a side opposite the container side of the cover plate, and an open side of the dome is sized and shaped to receive a design portion of a light bulb positioned centrally in a rubber grommet on a base end of the torodial fragrance container.

9. An aroma generator as claimed in claim 8, wherein the dome has select transparency to allow light to be transmitted from the light bulb through the dome.

10. An aroma generator as claimed in claim 1 and further comprising a means for protecting structural integrity of the toroidal fragrance container with non-heated sections circumferentially in the channel base.

11. An aroma generator as claimed in claim 10, wherein the means for protecting structural integrity of the toroidal fragrance container with non-heated sections circumferentially in the channel base is positioning of a design plurality of segments of the electrical-resistance heater circumferentially with a design distance between each of the segments of the electrical-resistance heater in the channel base,
   adjacent segments of the electrical-resistance heater intermediate terminal segments of the electrical-resistance heater are joined with electrical-conductors, and
   the terminal segments of the electrical-resistance heater are joined to conductor leads to an electrical source.

12. An aroma generator as claimed in claim 1 and further comprising a means for regulating amount of electrical current flow between a source of electrical current and the electrical-resistance heater in the channel base in the toroidal container channel of the toroidal fragrance container.

13. An aroma generator as claimed in claim 12, wherein the means for regulating amount of electrical current flow between a source of electrical current and the electrical-resistance heater in the channel base in the toroidal container channel of the toroidal fragrance container is positioning of a select number of resistors having a select resistance rating intermediate the source of electrical current and the electrical-resistance heater.

14. An aroma generator as claimed in claim 12, wherein the means for regulating amount of electrical current flow between a source of electrical current and the electrical-resistance heater in the channel base in the toroidal container channel of the toroidal fragrance container is a variable resistor having a design range of resistance capacity intermediate the source of electrical current and the electrical-resistance heater.

15. An aroma generator as claimed in claim 8 and further comprising a means for regulating amount of electrical current flow between a source of electrical current and the electrical-resistance heater in the channel base in the toroidal container channel of the toroidal fragrance container.

16. An aroma generator comprising a toroidal fragrance container having a toroidal container channel with a cylindrical inside wall, a cylindrical outside wall positioned a select distance outward radially from the cylindrical inside wall and a channel base extended radially intermediate a bottom of the inside wall and a bottom of the cylindrical outside wall,
   a cover plate maintained in a covering position over the toroidal container channel with a cylindrical attachment sleeve extended from a container side of the cover plate,
   at least one attachment appendage extended outward radially from an attachment end of the cylindrical attachment sleeve,
   at least one arcuate attachment channel in an inside periphery of the cylindrical inside wall has a linear entrance into which the attachment appendage is positioned and then rotated about the axis of the toroidal fragrance container by rotation of the cover plate to position the attachment appendage in the arcuate attachment channel where a wall of the arcuate attachment channel is intermediate the attachment appendage and the cover plate to prevent linear removal of the cover plate without opposite rotation before linear removal,
   an electrical-resistance heater in the channel base,
   a plurality of spacer ridges positioned radially on an attachment side of the cover plate to provide aroma-discharge passages between the cover plate and top edges of the toroidal channel,
   a means for attaching a light bulb of a select size to the toroidal fragrance container at a position radially inward from the cylindrical inside wall of the toroidal container channel with an attachment stem of the light bulb extended outward from the toroidal fragrance container for attachment to a light-bulb socket linearly to the axis of the toroidal fragrance container, a means for safety protection against heat and breakage of a light bulb positioned centrally in the torodial fragrance container, and a means for protecting structural integrity of the toroidal fragrance container with non-heated sections circumferentially in the channel base.

17. An aroma generator as claimed in claim 16 and further comprising a means for regulating amount of electrical current flow between a source of electrical current and the electrical-resistance heater in the channel base in the toroidal container channel of the toroidal fragrance container.

18. An aroma generator as claimed in claim 16, wherein the means for protecting structural integrity of the toroidal fragrance container with non-heated sections circumferentially in the channel base is positioning of a design plurality of segments of the electrical-resistance heater circumferentially with a design distance between each of the segments of the electrical-resistance heater in the channel base, adjacent segments of the electrical-resistance heater intermediate terminal segments of the electrical-resistance heater are joined with electrical-conductors, and the terminal segments of the electrical-resistance heater are joined to conductor leads to an electrical source.

19. An aroma generator as claimed in claim 16, wherein the means for attaching a light bulb of a select size to the toroidal fragrance container is a rubber grommet having an attachment aperture sized and shaped to receive the stem of the light bulb with desired tightness, and an outside periphery of the rubber grommet is attachable to an inside periphery of the toroidal fragrance container proximate a base end of the toroidal container channel.

20. An aroma generator as claimed in claim 19 and further comprising a bulb-attachment wall positioned at a design distance inward linearly from the base end of the toroidal container channel and extended inward radially a design distance to a bulb-attachment aperture, a rubber grommet positioned adjacent to the bulb-attachment wall and the inside periphery of the toroidal fragrance container, and a bulb-attachment aperture in the rubber grommet having an inside periphery concentric to the axis of the toroidal fragrance container for concentric positioning and retainment of the light bulb linearly to the axis of the toroidal fragrance container.

21. An aroma generator as claimed in claim 16, wherein the means for protection against heat and breakage of the light bulb positioned centrally in the torodial fragrance container is as a dome extended centrally from a side opposite the container side of the cover plate, and an open side of the dome is sized and shaped to receive a design portion of a light bulb positioned centrally in a base end of the torodial fragrance container.

22. An aroma generator as claimed in claim 21, wherein the dome has select transparency to allow light to be transmitted from the light bulb through the dome.

23. An aroma generator as claimed in claim 16, wherein the means for regulating amount of electrical current flow between a source of electrical current and the electrical-resistance heater in the channel base in the toroidal container channel of the toroidal fragrance container is positioning of a select number of resistors having a select resistance rating intermediate the source of electrical current and the electrical-resistance heater.

24. An aroma generator as claimed in claim 16, wherein the means for regulating amount of electrical current flow between a source of electrical current and the electrical-resistance heater in the channel base in the toroidal container channel of the toroidal fragrance container is a variable resistor having a design range of resistance capacity intermediate the source of electrical current and the electrical-resistance heater.

25. An aroma generator comprising a toroidal fragrance container having a toroidal container channel with a cylindrical inside wall, a cylindrical outside wall positioned a select distance outward radially from the cylindrical inside wall and a channel base extended radially intermediate a bottom of the inside wall and a bottom of the cylindrical outside wall, a cover plate maintained in a covering position over the toroidal container channel with a cylindrical attachment sleeve extended from a container side of the cover plate, at least one attachment appendage extended outward radially from an attachment end of the cylindrical attachment sleeve, at least one arcuate attachment channel in an inside periphery of the cylindrical inside wall has a linear entrance into which the attachment appendage is positioned and then rotated about the axis of the toroidal fragrance container by rotation of the cover plate to position the attachment appendage in the arcuate attachment channel where a wall of the arcuate attachment channel is intermediate the attachment appendage and the cover plate to prevent linear removal of the cover plate without opposite rotation before linear removal, an electrical-resistance heater in the channel base, a plurality of spacer ridges positioned radially on an attachment side of the cover plate to provide aroma-discharge passages between the cover plate and top edges of the toroidal channel, a bulb-attachment wall positioned at a design distance inward linearly from the base end of the toroidal container channel and extended inward radially a design distance to a bulb-attachment aperture, a rubber grommet positioned adjacent to the bulb-attachment wall and the inside periphery of the toroidal fragrance container, a bulb-attachment aperture in the rubber grommet having an inside periphery concentric to the axis of the toroidal fragrance container for concentric positioning and retainment of the light bulb linearly to the axis of the toroidal fragrance container, a dome extended centrally from a side opposite the container side of the cover plate, an open side of the dome is sized and shaped to receive a design portion of a light bulb positioned centrally in a base end of the torodial fragrance container, the dome has select transparency to allow light to be transmitted from the light bulb through the dome, a design plurality of segments of the electrical-resistance heater positioned circumferentially with a design distance between each of the segments of the electrical-resistance heater in the channel base, adjacent segments of the electrical-resistance heater intermediate terminal segments of the electrical-resistance heater are joined with electrical-conductors, and the terminal segments of the electrical-resistance heater are joined to conductor leads to an electrical source.

26. An aroma generator as claimed in claim 25 and further comprising a means for regulating amount of electrical current flow between a source of electrical current and the electrical-resistance heater in the channel base in the toroidal container channel of the toroidal fragrance container.

* * * * *